US00PP15014P3

(12) United States Plant Patent
Mann

(10) Patent No.: US PP15,014 P2
(45) Date of Patent: Jul. 13, 2004

(54) PLUM TREE NAMED 'MANN'

(50) Latin Name: *Prunus salicina*
Varietal Denomination: Mann

(76) Inventor: Bobby W. Mann, 3617 Skyline Dr., Warrior, AL (US) 35180

( * ) Notice: Subject to any disclaimer, the term of this patent is extended or adjusted under 35 U.S.C. 154(b) by 0 days.

(21) Appl. No.: 10/263,318

(22) Filed: Oct. 3, 2002

(65) Prior Publication Data

US 2004/0068774 P1 Apr. 8, 2004

(51) Int. Cl.[7] ..... A01H 5/00

(52) U.S. Cl. ..... Plt./184

(58) Field of Search ..... Plt./184

*Primary Examiner*—Anne Marie Grunberg
*Assistant Examiner*—Susan B. McCormick-Ewoldt
(74) *Attorney, Agent, or Firm*—Wm. Randall May

(57) ABSTRACT

The present invention relates to a new and distinct variety of Japanese plum tree (*Prunus salicina*) characterized by its large trunk and limbs, its resistance to disease and by its regular and abundant production of uniformly large and attractive fruit which is mature for harvesting beginning approximately mid-June and which has a distinctive flavor and an excellent storage life.

5 Drawing Sheets

Genus and species of new variety: *Prunus salicina.*
Denomination of new variety: 'Mann' Plum Tree.

BACKGROUND OF THE VARIETY

The present invention relates to a new and distinct variety of plum tree, (*Prunus salicina*), which will hereinafter be denominated varietally as the 'Mann' plum tree, and more particularly to a plum tree which produces, in abundance, a very large, uniform and attractive fruit. The fruit has a distinct flavor and is mature for commercial harvesting approximately mid-June under the ecological conditions prevalent to the north-central portion of the State of Alabama.

An interesting characteristic of the new variety is its large trunk and compact growth habit. Mature trees have trunk diameters averaging 9¾ inches and range in height from approximately 9 feet to approximately 11 feet. The average width of the new variety is approximately 10 feet. The limbs of mature trees of the new variety are also large having diameters ranging from 3 inches to 4¾ inches measured at a point 12 inches from the trunk.

Another interesting characteristic of the new variety is its resistance to canker and other diseases of the bark and wood.

Another interesting characteristic of the new variety is the virtually virus-free character of the fruit thereby allowing the fruit to be cold stored for long periods of time without discoloration and without additives.

Another interesting characteristic of the new variety resides in its prolific production of fruit. Plums produced by the new variety grow in clusters with mature trees producing between 18 and 32 eight-quart baskets of fruit per season.

Another interesting characteristic of the new variety is the frost resistant character of its blossoms. Trees of the new variety will generally re-bloom after a hard frost.

Another interesting characteristic of the new variety is its extended harvest period. The fruit of the new variety generally matures in mid-June of each year and may be harvested through mid-July.

These and other characteristics make the new variety distinct from known varieties of *Prunus salicina.*

ORIGIN AND ASEXUAL REPRODUCTION OF THE NEW VARIETY

The present variety of the 'Mann' plum tree was discovered by the inventor, Bobby W. Mann, in 1988. The new variety was discovered as a chance seedling within the cultivated area of Mr. Mann's orchard in Blount County near Warrior, Ala. The new variety was successfully asexually reproduced by Mr. Mann in 1998 by budding the new variety onto the rootstock of a Halford peach seedling. The resulting asexually reproduced trees have been observed by the inventor since that time and it has been confirmed that the distinctive characteristics of the original parent tree of the new variety are, in all respects, expressed in the asexually reproduced trees.

SUMMARY OF THE NEW VARIETY

A new and distinct variety of plum tree named the 'Mann' plum tree is described. The variety is characterized by its large trunk and limbs, compact growth habit and by the regular production of large, firm, attractive fruit. The fruit produced by this new variety is very large, is fully rounded in shape, has bright yellow-green skin coloration, and possesses an excellent flavor. The large size of the fruit and relative small pit size produces an abundance of edible, good flavored, flesh. It has been determined that the new variety fruit can be harvested beginning approximately mid-June and has an excellent storage life. The asexually reproduced plum tree of the present invention is hearty and will produce a heavy crop of fruit that is easy to harvest. It has also been determined that the blossoms of the variety are frost resistant as compared to other varieties of Japanese plum.

BRIEF DESCRIPTION OF THE PHOTOGRAPHS

Other distinctive characteristics of the new variety are exemplified in the accompanying color photographs wherein.

DETAILED DESCRIPTION OF THE NEW VARIETY

Figure 1:
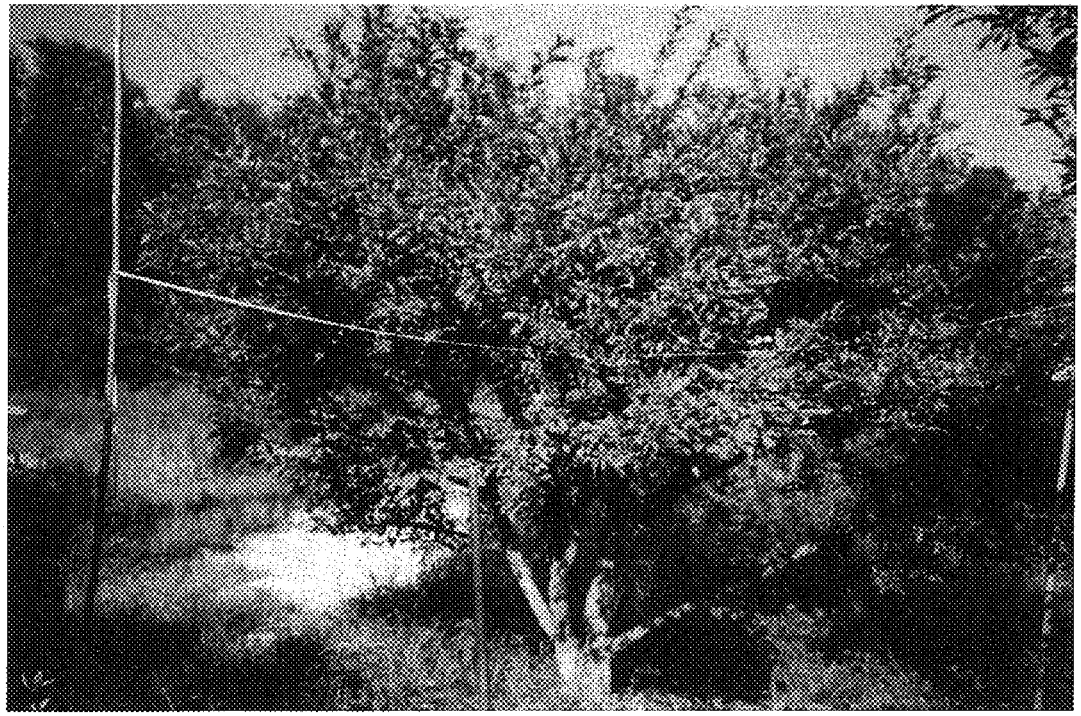
FIG. 1 shows an adult parent tree—age 14 years.
Figure 2:
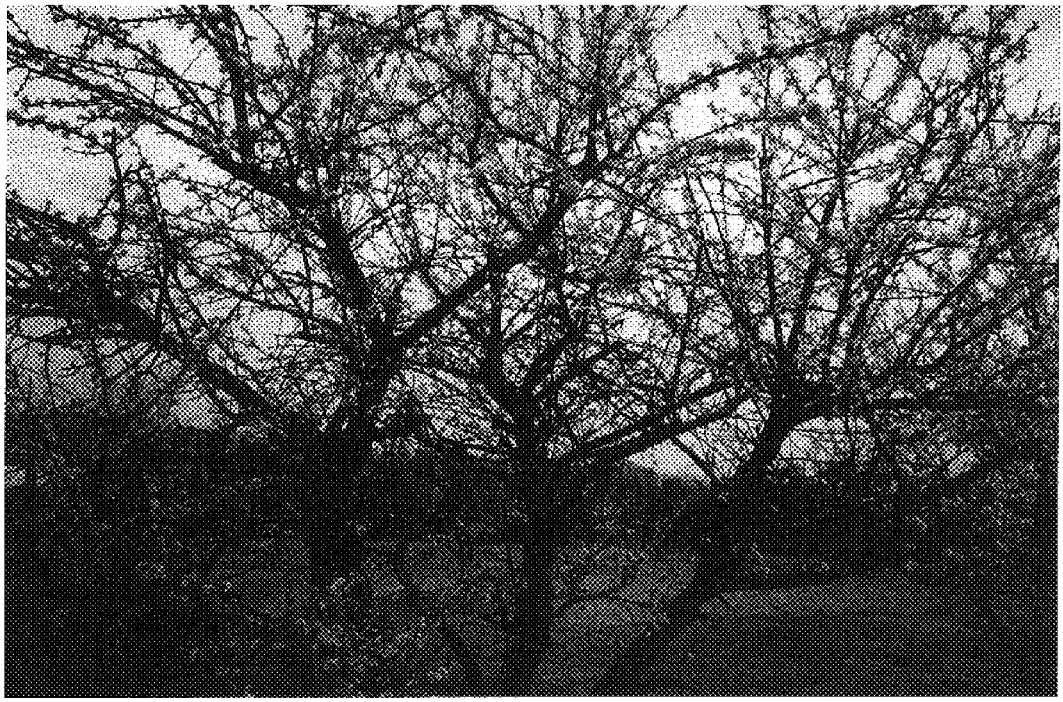
FIG. 2 shows the adult parent tree of FIG. 1 with adult inflorescence.
Figure 3:
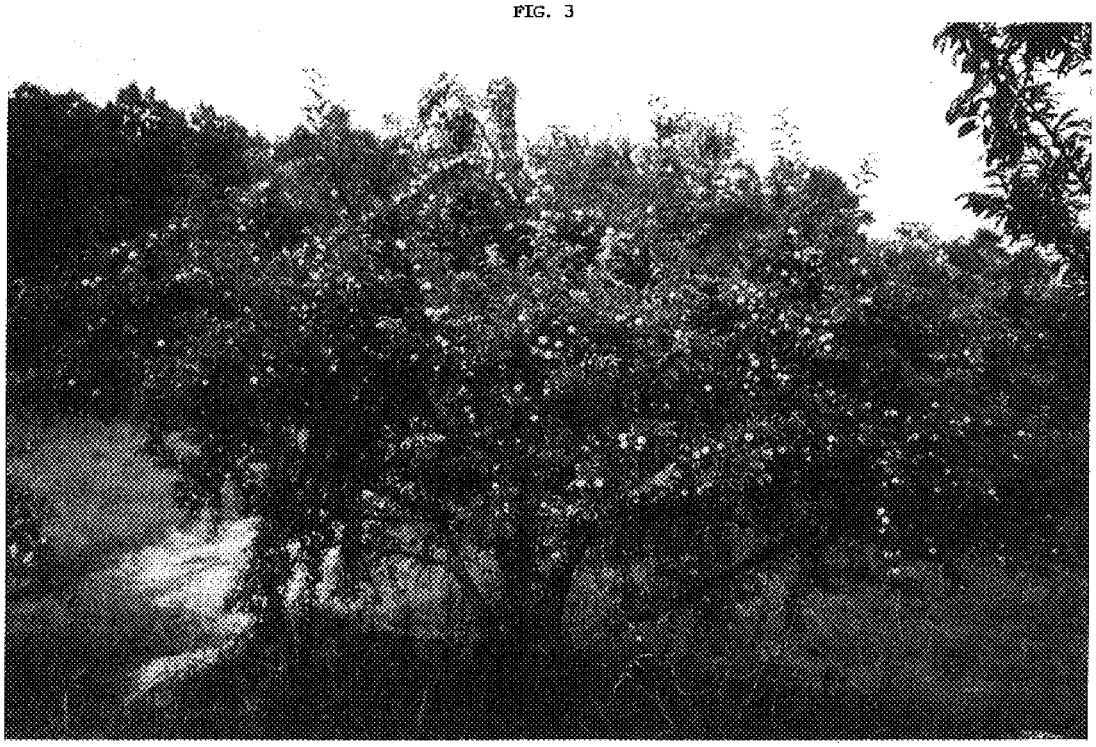
FIG. 3 shows the adult parent tree of FIG. 1 bearing fruit.
Figure 4:
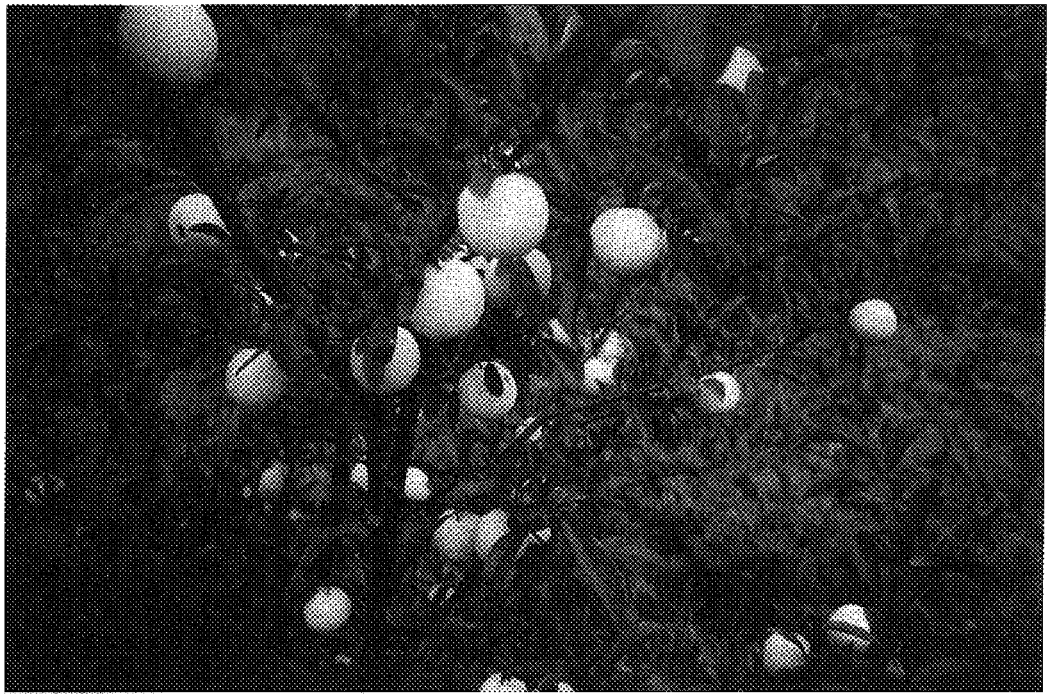
FIG. 4 shows a close up of a branch with adult leaves and bearing mature fruit of the new variety.
Figure 5:
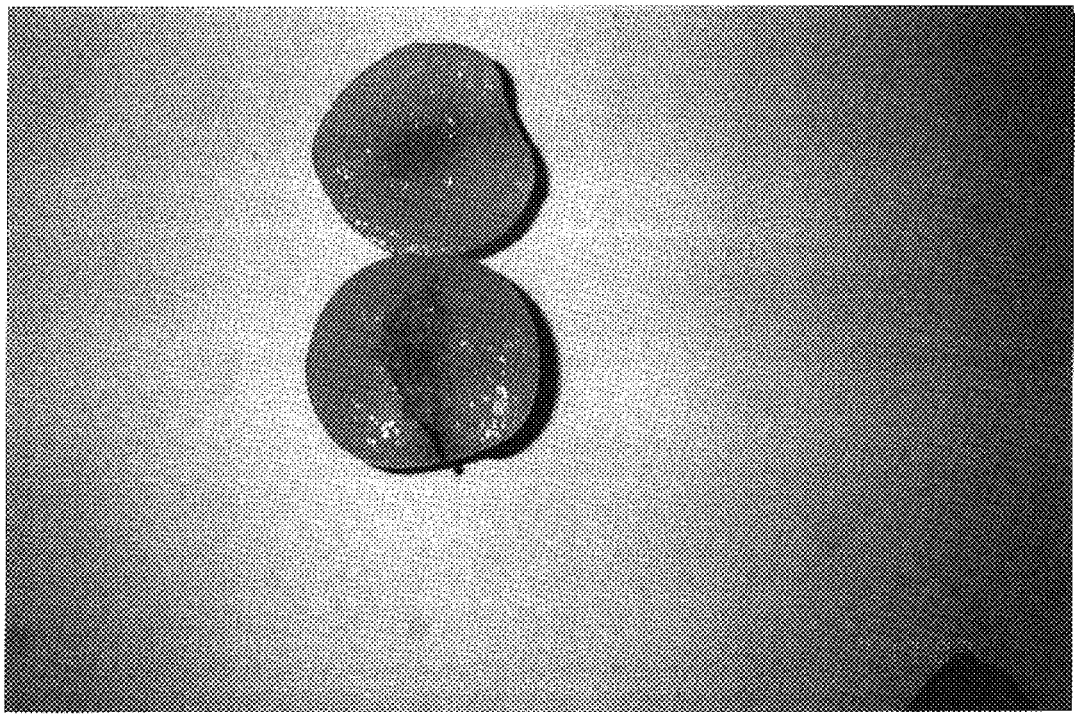
FIG. 5 shows mature fruit sectioned and laid open with the stone and stem left in place in one section and the stone removed to expose the pit cavity in the other section.

The following is a detailed botanical description of 'Mann' plum tree, its flowers, foliage and fruit based on observations of specimens grown in Blount County near Warrior, Ala. at the orchard of origin. All major color-code designations are by reference to the Pantone Book of Color published in 1990 by Harry N. Abrams, Inc., N.Y. Common color names are also occasionally employed.

Tree:

*Generally.*—Age of observed parent tree — 14 years. Size — Large and in the upper range for a Japanese plum. Vigor — Very vigorous and in the upper range for a Japanese plum. Chilling Requirements — 400 to 750 hours. Figure — Bushy tree to height of eleven feet and ten feet wide. Productivity — Very productive; large size plum, typically formed in clusters on numerous spurs. Average of 455 pounds per tree in year 2000. Regularity of Bearing — Regular, good annual crop.

Trunk:

*Size.*—Large and in the upper range for a Japanese plum. Typical diameter of trunk is approximately 9¾ inches (24.765 cm) measured at a height of 12 inches (30.48 cm) from soil level.

*Surface.*—Smooth to medium rough.

*Color.*—Sand (Pantone 15-1225).

Branches:

*Size.*—Medium diameters as scaffold branches are in the medium range for a Japanese plum. Typical branch diameters range from 3 inches (7.63 cm) to 4¾ inches (12.065 cm) measured at a distance of 12 inches (30.48 cm) from the trunk.

*Surface texture.*—Mature branches appear slightly rough and immature branches appear smooth.

*Lenticels.*—Medium number and in the middle range for a Japanese plum. Average number of lenticels per circumferential inch is approximately 115; length and width of lenticels range between 7/32 inch (5.55 mm)×1/16 inch (1.59 mm) to 29/32 inch (23.02 mm)×¼ inch (6.35 mm).

*Lenticel color.*—Inca Gold (Pantone 17-1048).

Leaves:

*Type/size.*—Dicot/Large. 4¼ inch (107.95 mm) length, 1¾ inch (44.45 mm) wide.

*Form/shape.*—Ovate with acuminate tip.

*Margin.*—Very finely serrated.

*Surface.*—Upper, reticulate; lower, medium veined. Venation: simple pinnate pattern having a main leaf vein with long unbranched leaf veins which turn and run substantially parallel to the leaf margin at the edge of the leaf. Vein color: main vein on lower surface is Shamrock (Pantone 15-6432).

*Thickness.*—Medium and in the middle range for a Japanese plum.

*Texture.*—Glabrous.

*Petiole.*—Medium size, medium length, medium thickness. Length: from approximately 0.344 inch (8.73 mm) to 0.437 inch (11.11 mm). Diameter: from approximately 0.044 inch (1.12 mm) to 0.048 inch (1.22 mm). Color: Green Banana (Pantone 14-0434).

*Glands.*—No glands found on stem.

*Color.*—Upper, Cactus (Pantone 18-0130); lower, Jade Green (Pantone 16-0228).

Flower buds:

*Size.*—Medium. Diameter: approximately 0.052 inch (1.32 mm). Circumference: approximately 0.163 inch (4.14 mm).

*Length.*—Medium. Average length: 0.181 inch (4.60 mm).

*Form.*—Plump-free.

*Surface texture.*—Glabrous.

*Color.*—Lily Green (Pantone 13-0317).

Flowers:

*Blossom/bloom period.*—About 12 to 14 days. Ranging generally from March 12 to March 26 at Blount County, Ala.

*Quantity.*—Abundant. Number of flower buds per node ranging from 2 to 4.

*Size.*—Medium. Flower diameter — From 0.7086 inch (18 mm) to 0.9055 inch (23 mm) for fully open bloom.

*Petals.*—Five in number and of medium size. Average petal length is 0.394 inch (10 mm), average width is 0.276 inch (7 mm). The petal form is slightly variable from oval to ovate having and obtuse apex and a cuneate base. The petals have a smooth, wavy margin somewhat ruffled near apex.

*Sepals.*—Five in number and of medium size. Alternately arranged to petals. Average length: 0.156 inch (3.962 mm); Average width: 0.125 inch (3.175 mm) Color: Mellow Green (Pantone 12-0426).

*Pedicel.*—The pedicel is 0.197 to 0.236 inch (5 to 6 mm) in length, slightly less than 0.039 inch (1 mm) diameter, and Mellow Green (Pantone 12-0426).

*Pollen.*—Semi self-fertile. Abundant. Pollen color is bright yellow, Buttercup (Pantone 12-0752).

*Stamens.*—Number varies from 30 to 44 per flower. Average length 0.297 inch (7.544 mm). Filament color is white. Anther color is bright yellow, Buttercup (Pantone 12-0752).

*Flower color.*—White.

*Pistils.*—One. Average length 0.406 inch (10.312 mm). Color: Sunshine (Pantone 12-0727). Stigma color is Citron (Pantone 12-0524).

*Aroma.*—No characteristic fragrance noted.

Fruit:

*Generally.*—Maturity — Fruit matures from the 3rd week of June to approximately July 10 at Blount County, Ala. Size — Medium to large. Average diameter axially 50.5 mm; average diameter transversely in suture plane 49.5 mm. Weight — 2.5 to 3 ounces each (78 to 93 grams). Form — Very good uniformity; shape nearly globose, slightly flattened at stem end. Suture — Generally very shallow; inconspicuous line extends from base to the apex and is slightly deeper at cavity. Base — Nearly round, slightly flat. Apex — Slightly rounded. Cavity — Rounded, appx. 5 mm depth. Stem — Average length appx. 13 mm. Ventral Surface — Generally smooth, rounded.

*Flesh.*—Texture — Smooth, juicy and crisp at harvest time. Fibers — Very small and tender. Flavor or Eating Quality — Flavor — good. Eating quality — good. Juice — Slight to moderate. Aroma — Slight. Color — Cadmium Yellow (Pantone 15-1054). Ripening — Even ripening throughout fruit.

*Skin.*—Thickness — Medium and in the middle range for a Japanese plum. Texture — Medium and in the middle range for a Japanese plum. Bloom (wax) — Moderate and easily rubbed leaving shiny surface. Tendency to Crack — None observed. Taste — Tart. Color — Amber Yellow (Pantone 13-0942).

*Stone.*—Type — Cling stone. Size — Length appx. 19 mm; thickness appx. 9.5 mm. Form — Oval. Base — Flat. Apex — Very slight point. Sides — Generally equal. Surface — Relatively smooth and slightly uneven. Ridges — None. Tendency to Split — Not evident. Color — Orange Ochre (Pantone 16-1253).

Use: Fresh fruit market.

Market: Local and long distance.

Keeping and shipping quality: Good to excellent. Fruit remained firm after 14 days out of cool storage.

Resistance to disease: Resistance to canker as compared to other varieties of Japanese plum has been noted. No disease observed to date.

Although the new variety of plum tree described herein possesses the described characteristics noted above as a result of the ecological conditions prevailing in Blout County near Warrior, Ala., it is to be understood that these characteristics may vary slightly due variations in climate, soil conditions, irrigation, fertilization, pruning, pest control, and the like.

What is claimed is:

1. A new and distinct variety of plum tree substantially as illustrated and described, characterized by its large trunk and limbs, compact growth habit and being a regular and productive bearer of uniformly large, firm, attractive clingstone fruit with good flavor and an abundance of edible flesh; the fruit is further characterized by its resistance to disease and by being mature for commercial harvesting and shipment approximately the third week of June under the ecological conditions prevalent to the north-central portion of the State of Alabama.

* * * * *